United States Patent
Purdy

(10) Patent No.: US 8,188,142 B2
(45) Date of Patent: May 29, 2012

(54) POLYMERS FROM PROPENYL ETHER MONOMERS

(75) Inventor: Andrew P Purdy, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 858 days.

(21) Appl. No.: 12/174,232

(22) Filed: Jul. 16, 2008

(65) Prior Publication Data

US 2009/0182155 A1    Jul. 16, 2009

Related U.S. Application Data

(60) Provisional application No. 61/021,419, filed on Jan. 16, 2008.

(51) Int. Cl.
*A61K 31/381* (2006.01)
*C07D 333/48* (2006.01)

(52) U.S. Cl. .......................... 514/445; 549/67

(58) Field of Classification Search .................. 514/445; 549/67

See application file for complete search history.

(56) References Cited

U.S. PATENT DOCUMENTS 2,419,082 A    4/1947 Morris et al.
5,385,958 A    1/1995 Bachmann et al.

OTHER PUBLICATIONS

Price et al., "Solvent Effects in Base-Catalyzed Isomerization of Allyl to Propenyl Ethers" J. Am. Chem. Soc., 83(7), 1773 (1961).

Crivello et al., "Efficient Isomerization of Allyl Ethers and Related Compounds Using Pentacarbonyliron" J. Org. Chem., 63, 6745-6748 (1998).
Crivello et al., "Transition Metal-Catalyzed Isomerization and Polymerization of Allylic and Enolic Ethers" J. Polym. Sci. A: Polym. Chem., 35, 2521-2532 (1997).
Crivello et al., "Synthesis and Photopolymerization of 1-Propenyl Ether Functional Siloxanes" Chem. Mater., 8, 209-218 (1996).
Purdy et al., "Synthesis and Polymerization of Sulfolane-3-propenyl Ether" ACS Meeting Proceedings (Jan. 22, 2007).
Purdy et al., "Synthesis and Polymerization of Sulfolane-3-propenyl Ether" ACS Meeting (Mar. 29, 2007).

*Primary Examiner* — Taofiq A Solola
(74) *Attorney, Agent, or Firm* — Amy L. Ressing; Joseph T. Grunkemeyer

(57) ABSTRACT

The compounds shown below. R is —O—, —O—$(CH_2)_n$—O—, or —(O—$CH_2$—$CH_2)_n$—O—; and n is a positive integer. Heating an allyl ether compound in the presence of $Fe(CO)_5$ and a base to form the below propenyl ether monomer. Polymerizing the below propenyl ether monomer.

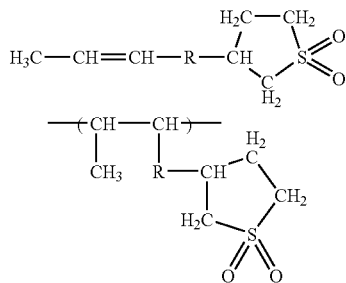

18 Claims, 3 Drawing Sheets

… …

POLYMERS FROM PROPENYL ETHER MONOMERS

This application claims the benefit of U.S. Provisional Patent Application No. 61/021,419, filed on Jan. 16, 2008. This provisional application and all other referenced publications and patent documents are incorporated herein by reference.

FIELD OF THE INVENTION

The invention is generally related to propenyl ether monomers and polymers made therefrom.

DESCRIPTION OF RELATED ART

Most ordinary polymeric materials have dielectric constants in the 2-4 range, although some are known to be quite a bit higher (Bartnikar et al, Editors "Engineering Dielectrics, Volume IIA" ASTM special technical publication 783 (1983)). New high dielectric materials are of interest for capacitor applications. One way of obtaining a high dielectric constant at low-frequency is by using highly polar pendant groups that can rotate to align with the electric field (Zhu et al., *Macromolecules*, 27, 4076 (1994); Cardoso et al., *J. Polym. Sci. B Polym. Phys.*, 35, 479-488 (1997); Purdy et al., *Polymer Preprints*, 44, 854 (2003)). Use of cheap and easily obtainable monomers may help a technology to be viable. A catalytic method was reported for isomerizing allyl ethers into much more readily polymerizable propenyl ethers (Crivello et al., *J. Org. Chem.*, 63, 6745 (1998). The method involves treatment of the allyl ether with Fe(CO)$_5$ in the presence of base.

SUMMARY OF THE INVENTION

The invention comprises a compound comprising the formula of Eq. (1). R is —O—, —O—(CH$_2$)$_n$—O—, or —O—CH$_2$—CH$_2$)$_n$—O—; and n is a positive integer.

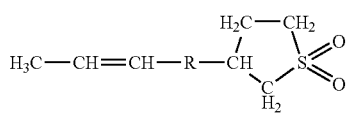

(1)

The invention further comprises a compound comprising the formula of Eq. (2).

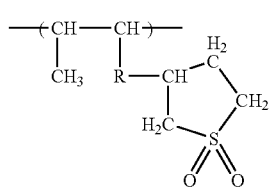

(2)

The invention further comprises a method comprising: providing an allyl ether compound comprising the formula of Eq. (3); and heating the allyl ether compound in the presence of Fe(CO)$_5$ and a base to form a propenyl ether monomer comprising the formula of Eq. (1).

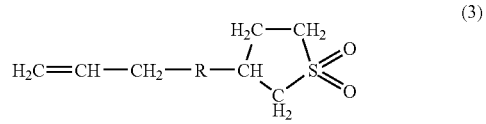

(3)

The invention further comprises a method comprising: polymerizing a propenyl ether monomer comprising the formula of Eq. (1).

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

As an allyl ether of the highly polar sulfolane moiety may prepared from inexpensive starting materials (Purdy et al., *Polymeric Materials: Science and Engineering*, 84, 641 (2001); Morris et al., U.S. Pat. No. 2,419,082 (1947)) allyloxysulfolane 1 may be isomerized into propenyloxysulfolane 2. The isomerization may be by, for example, treatment with Fe(CO)$_5$ in the presence of base, treatment with KOCMe$_3$ in appropriate solvents, or treatment with Ru catalysts. The cationic polymerization of 2 using both photoactivated initiators and BF$_3$(OEt$_2$) has been investigated. Some dielectric properties of poly(propenyloxysulfolane) 3 have been measured.

Polypropenyl ethers with sulfolane and other highly polar pendant groups have some promise as capacitor materials. The ability of the monomer to coordinate and solubilize metal salts is also a clue that these materials could have promise as a component of composites with ferroelectric nanoparticles.

Probably as a result of the high polarity of 2, this propenyl ether is a very good solvent for the iron carbonyl salt and byproducts of the isomerization reaction, and the presence of iron carbonyl compounds may lead to decomposition during distillation. Good purification by distillation may be achieved if the metal salts are removed first. Extraction with a saturated solution of NH$_4$Cl which the mixture is exposed to air may oxidize and remove the iron carbonyl salts, but is very slow, especially when large quantities are involved. Copper(II)

salts such as CuCO₄ may work to remove the iron by oxidation to Fe(II), but the highly polar 2 is also a very good solvent for the resulting Cu(I) salts which slowly oxidize to Cu(II) in air. The presence of small amounts of Cu salts may not inhibit distillation, but large amounts may result in decomposition during distillation.

Figure 1:
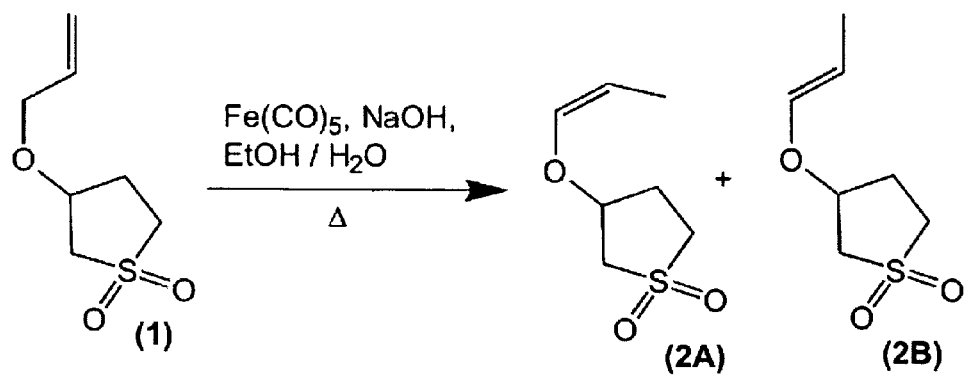
FIG. 1 shows isomerization of 1 to the cis (2A) and trans (2B) isomers of 2.

The purified monomer may be a mixture of both cis and trans isomers as pictured in FIG. 1. Polymerization may be effected through either photoinitiated cationic initiators or the traditional cationic initiator BF₃(OEt₂). The photoinitiation may be done with neat monomer or in solutions of monomer in, for example, sulfolane. In both cases a mixture of low molecular weight and higher molecular weight material may result. Concentrated solutions of sulfolane may result in a higher polymer yield than neat monomer. The polymer may be separated from low molecular weight oligomers by dissolving the product in, for example, a sulfolane/(CH₂Cl₂ or CHCl₃) mixed solvent and slowing adding the solvent to rapidly stirred ethanol to precipitate the polymer. Further purification may be affected by dissolving the polymer in sulfolane and precipitating it by slow addition to rapidly stirred water. The purification in water may help to avoid depolymerization over several months, possibly due to residual acidic impurities. High steric interaction between pendant groups may make depolymerization relatively easy. Putting a spacer between the chain and sulfolane group could reduce steric interaction. The spacer may be an alkyl chain or a polyethylene glycol chain having one or more repeat units. The monomer with a spacer may be made by reacting an allyl ether alcohol that includes the spacer (such as CH₂=CH—CH₂—(O—CH₂—CH₂)ₙ—OH or CH₂=CH—CH₂—O—(CH₂)ₙ—OH) with 3-sulfolene.

One problem with some highly polar polymers is dielectric losses. A high loss may make a material unsuitable for capacitors, regardless of its dielectric constant. Capacitors may also require a material with high breakdown strength. The polymer 3 may have a dielectric constant of ~6-7 at 1 kHz with a dissipation factor of <0.01. Such a low dissipation factor is noteworthy for a material containing highly polar groups.

Having described the invention, the following examples are given to illustrate specific applications of the invention. These specific examples are not intended to limit the scope of the invention described in this application.

EXAMPLE 1

Synthesis of propenyloxysulfolane—Materials: Allyl alcohol, 3-sulfolene, sulfolane, sodium hydroxide, ammonium chloride, triarylsulfonium hexafluorophosphate 50% solution in propylene carbonate, boron trifluoride etherate, and iron carbonyl were obtained from Aldrich. Copper sulfate and ammonium hydroxide was obtained from Fisher. The synthesis of 1 was described previously (Purdy et al., *Polymeric Materials: Science and Engineering*, 84, 641 (2001); Morris et al., U.S. Pat. No. 2,419,082 (1947)). Generally, allyl alcohol (CH₂=CH—CH₂OH) was reacted with 3-sulfolene, catalyzed by a case such as sodium hydroxide. Sulfolane was purified by vacuum distillation from KOH pellets. Water was triple distilled, and ethanol was 200 proof, USP grade.

Instrumentation: Proton and ¹³C NMR spectra were recorded on a Bruker Avance-300 spectrometer using the carbon or residual proton peak of deuterated solvent as an internal reference. IR spectra were recorded on a FTIR spectrometer using KBr plates.

Isomerization of 1 to 2: A mixture of 1(134 g, 760 mmol), H₂O (10 mL), EtOH (150 mL), and NaOH (2.08 g, 52 mmol), was stirred under N₂. Fe(CO)₅ (5.0 g, 25.5 mmol) was added by syringe, and the mixture refluxed for 3 h under N₂. Upon cooling, the dark red mixture was extracted with ether and washed with saturated NH₄Cl, and after several days was stirred in a beaker to oxidize Fe compounds. A portion was treated with 6 g CuSO₄ dissolved in water to finish the Fe oxidization, extracted with ether, dried with MgSO₄, filtered, and fractionally distilled under dynamic vacuum. Initially, the pressure was high from decomposition products which were collected in the yellow forerun. The receiving flask was switched to collect product when distillate was clear and pressure had dropped below 35 mTorr, 13.5 g 2 was collected at 110° C., and used for the radical polymerization experiment. The remaining portion of crude product was treated with 22 g CuSO₄ and distilled in a similar manner affording 46.3 g 2. Total yield 59.8 g (45%). NMR: ¹H 5.99 (q), 5.95(q), 5.83(q), 5.81(q) (O—CH=C), 4.85 (m) (C=CH), 4.56 (m, C=CH and ring C—H), 3.17, 3.04 (m, SO₂CH₂), 2.36 (m, CH₂), 1.50 (m, CH₃). ¹³C: 143.2 (cis), 142.1 (O—CH=), 106.0, 103.8 (cis) (C=CH—), 76.0 (cis), 74.0 (CH—O), 56.8 (cis), 56.4 (SO₂CH₂CH), 49.2 (cis), 49.0 (SO₂CH₂CH₂), 29.3 (cis), 28.9 (SO₂CH₂CH₂), 12.4 (trans-CH3), 9.3 (cis-CH3). IR: 3622 (w), 3542 (w), 3040 (m), 3013 (m), 2953 (m), 2925 (m), 2893 (m), 2864 (m), 1669 (s), 1444 (m), 1404 (s), 1309 (vs), 1269 (s), 1220 (m), 1190 (s), 1123(vs), 1065 (s), 995 (m), 942 (m), 925 (m), 908 (m), 836 (w), 748(m), 684 (m), 654 (m), 623 (w), 571 (m), 475 (w), 438(m).

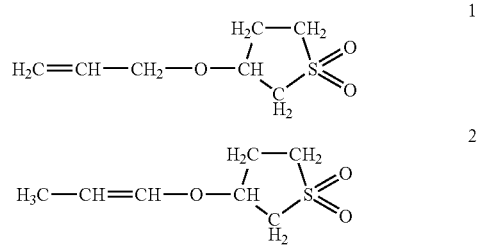

Figure 2:
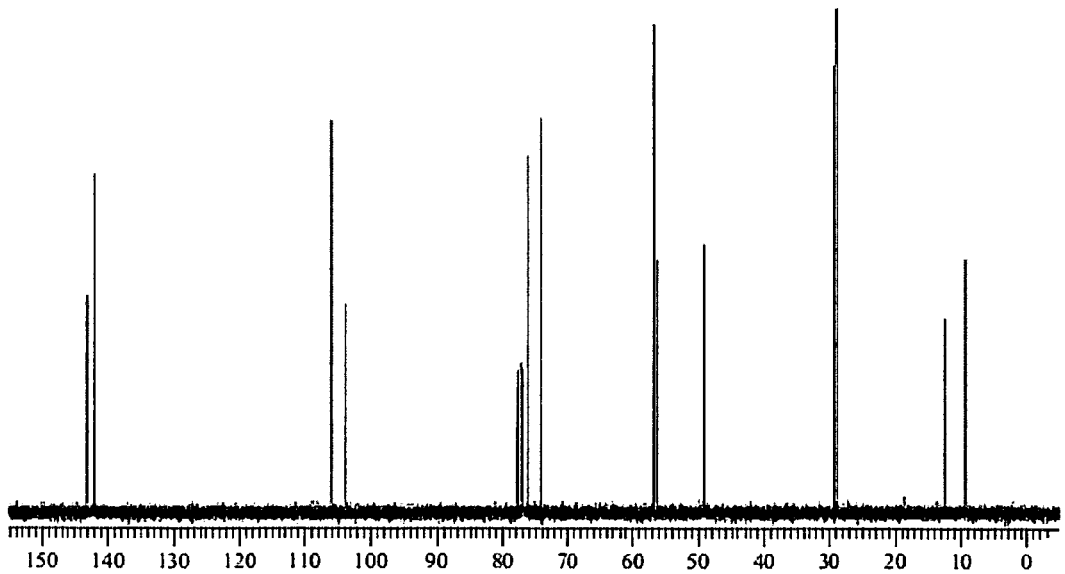
FIG. 2 shows a $^{13}$C NMR spectrum of distilled monomer 2 in CDCl$_3$.

The isomerization of allyloxysulfolane to propenyloxysulfolane (FIG. 1) was nearly quantitative with few side products as evidenced by NMR of the crude reaction mixture. The presence of Fe carbonyl compounds, which are highly soluble in the product and thus not removed by simple aqueous extraction, caused decomposition during distillation and impure distillates. Apparently, the ether linkage was being cleaved, and 2-sulfolene distilled with the product as identified by NMR. The previous report describing the general isomerization reaction gave no indication that this would be a problem, but did mention that the isomerized products were unstable on chromatographic columns, and could be susceptible to hydrolysis (Crivello et al., *J. Org. Chem.*, 63, 6745 (1998)). One explanation is that the sulfolane moiety solubilizes the Fe carbonyl compounds much more efficiently than the less polar substrates that were previously described. Washing the crude product with saturated NH₄Cl solution in air did slowly remove the iron to the aqueous phase, but was too slow to be practical on a large scale. A combination of air oxidation and treatment with copper sulfate solution rapidly oxidized the iron and allowed extraction of the iron to an aqueous phase. However, the copper (I) and (II) salts produced are also very soluble in 2. The first time CuSO₄ was used the distillation proceeded without incident and produced a 45% yield, but the second time there was decomposition during distillation affording a distillate of primarily 3-sulfolanol. In the latter case, the CuSO₄ was added while the product mixture was still alkaline. Washing organic extracts with NH$_4$OH until the aqueous extract is colorless is an effective way to remove the copper. According to the NMR spectrum (FIG. 2), the cis and trans isomers of 2 are present in about equal amounts.

Photopolymerization of 2—The monomer was mixed with 1-3 drops of triarylsulfonium hexafluorophosphate solution, either neat or in sulfolane, closed in either a Pyrex vial or a quartz tube, and irradiated with either a longwave UV lamp (~350-370 nm) or a 75 W arc lamp for the specified amount of time as indicated in Table 1.

TABLE 1

Photopolymerization reactions.

| # | 2 (g) | Sulfolane | initiator | irradiation, ° C. | Yield 3 |
|---|---|---|---|---|---|
| JP-30-A | 6.60[a] | none | 0.02 g | arc, 30 min | 2.3 g |
| JP-30-C | 6.60[c] | none | 0.04 g | arc, 30 min | 1.7 g |
| JP-30-D | 3.01[b] | none | 0.06 g | 1w UV, 3 d | low |
| 53R#1 | 2.13[c] | 1.17 g | 0.02 g | 1w UV, 15 h | 1.23 g |
| 53R#2 | 2.39[c] | 0.69 g | 0.01 g | 1w UV, 21 h | 1.94 g |
| 53R#3 | 2.53[c] | 0.50 g | 0.01 g | 1w UV, 3 d | 2.32 g |

[a]quartz tube
[b]Pyrex vial (2 dm)
[c]Pyrex vial (10 mL)

Cationic polymerization of 2 with BF$_3$(OEt$_2$)—A stirred mixture of dry sulfolane (12 g), dry CH$_2$Cl$_2$ (33 g), and 2 (9.52 g) was cooled to −50° C. with dry-ice/ethanol under an N$_2$ atmosphere Approximately 0.13 mL of a ~10% solution of BF$_3$(OEt$_2$) was injected into the stirred solution, and the mixture was allowed to warm up naturally. At about 0° C. the solution turned yellow, and after stirring for ~24 h at room temperature the solution was bright magenta. The polymer solution was added dropwise to EtOH with rapid stirring, and a yellowish white polymer precipitated. The precipitate was isolated by filtration, washed with water and ethanol, and dried under dynamic vacuum at 130° C. to remove residual sulfolane, affording 7.25 g (76%) of yellow 3.

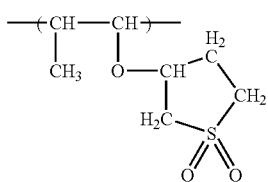

3

Purification of poly(propenyloxysulfolane) (3)—The polymer from the photopolymerization reactions was dissolved in sulfolane/CH$_2$Cl$_2$ and added dropwise to EtOH with rapid stirring. The precipitate was isolated by filtration, redissolved in sulfolane with heating, and added dropwise to triple distilled water with rapid stirring, washed with H$_2$O and EtOH, and dried under vacuum. The polymer precipitated from a CH$_2$Cl$_2$ solution of JP-30-A in EtOH was partially dissolved in acetone, and the acetone insoluble fraction was dried, dissolved in sulfolane, and precipitated dropwise in rapidly stirred water, affording 0.70 g polymer.

Polymerization of 2 was attempted by several methods. In line with expectations, radical polymerization using AIBN did not work, but cationic methods were effective. Initially, the monomer was photopolymerized neat in vials using a triarylsulfonium initiator. During polymerization, the material turned brown, and shrunk and cracked. Attempts to cut the polymer into slices with a diamond saw resulted in extremely fragile slices that either broke during cutting, or absorbed water from the air and liquefied. NMR shows the presence of monomer and low MW oligomers in which the polymer is apparently quite soluble, which explains the poor physical properties. Photopolymerized material is soluble in CH$_2$Cl$_2$, and when dripped into EtOH with stirring, the polymer precipitates, leaving the small oligomers in solution. Once purified of the lowest MW impurities, the polymer no longer dissolves in CH$_2$Cl$_2$ or CHCl$_3$, but remains highly soluble in sulfolane, an example of the principle that like dissolves like. Somewhat better photopolymerization results were obtained by diluting the monomer with sulfolane so that the polymerizing mixture remains liquid longer and reduces the amount of liquid oligomers in the final product. It was necessary for the polymer to have a final precipitation from water for the product to have long term stability. Otherwise it decomposed on a timescale of weeks to months. Presumably, this was due to the water removing acids from the polymer mixture that act as cationic initiators. The unzipping of the polymer in the presence of acids was probably due to steric effects of the sulfolane group directly attached to the ether oxygen, and suggests a possible use as a photoresist. In fact, the polymer decomposed readily when treated with strong acids.

The polymers were partially soluble in acetone, and it is likely that the acetone insoluble fractions were of higher molecular weight.

Figure 3:
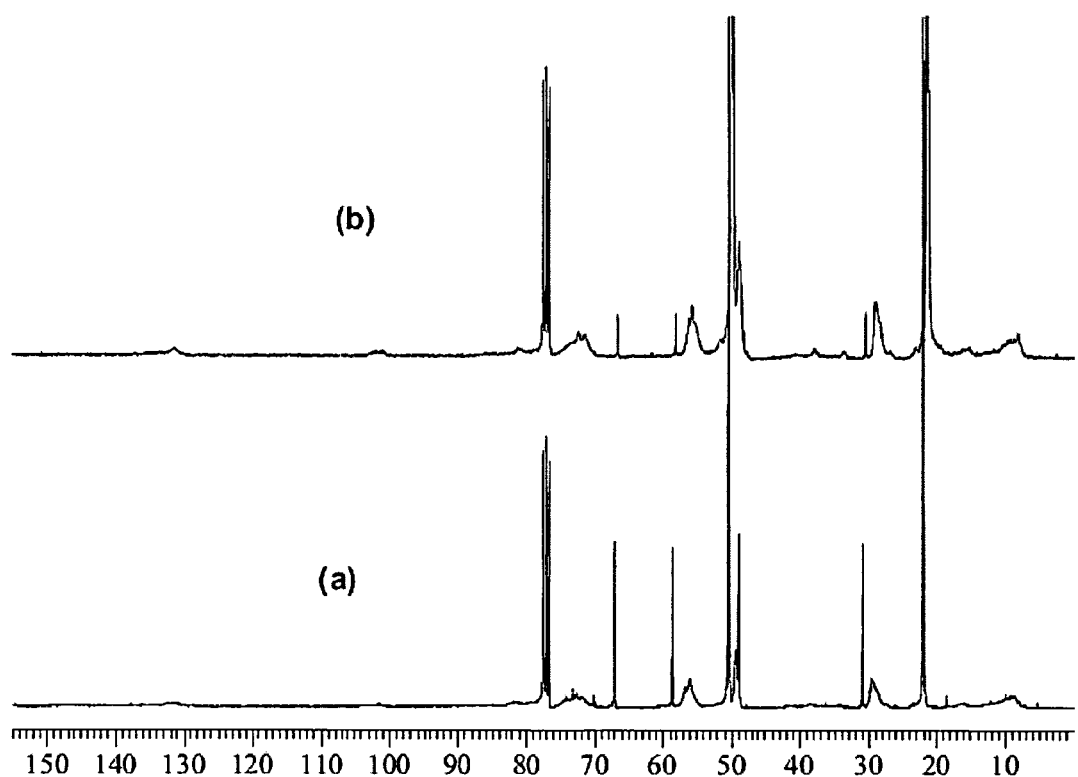
FIG. 3 shows $^{13}$C NMR spectra of polymers in CDCl$_3$/sulfolane. (a) Crude product from photopolymerization 53R#1. (b) BF$_3$(OEt)$_2$ initiated polymer, purified by precipitation. Off-scale peaks are from the sulfolane solvent.

Polymerization was also initiated with BF$_3$(OEt$_2$) in a sulfolane/CH$_2$Cl$_2$ solution. NMR spectra of CDCl$_3$/sulfolane solutions of polymer are shown in FIG. 3. The sharp lines not from solvent peaks are probably from small oligomers. The two very small broad peaks in the olefin region are attributable to unpolymerized end groups, which show that the average MW is low.

Dielectric measurements—Polymer discs for measurement were prepared by pressing powder in a 13 mm die at ~5000 lbs. The dielectric constants and loss factors were measured with the samples pressed between parallel plates using a HP 4284A instrument between 102 and 106 Hz, and a HP 4291A complex impedance analyzer between 106 and 1.8×109 Hz. Measurements at 1 kHz were also made with a BK-precision capacitance meter.

Figure 4:
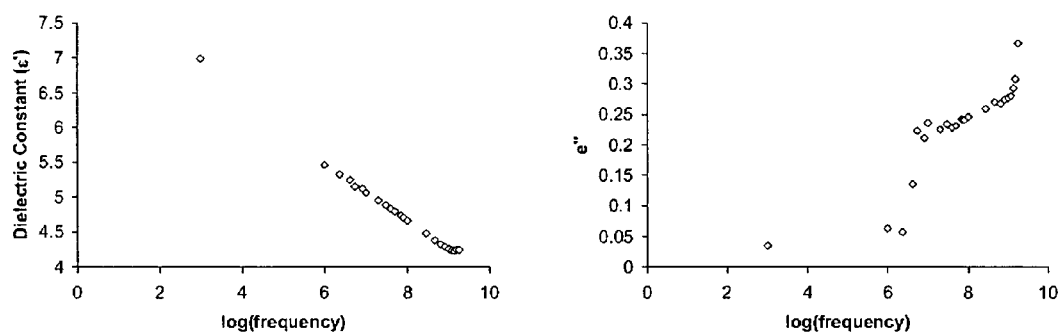
FIG. 4 shows dielectric constant ($\in'$) and loss factor ($\in''$) of 3 as a function of frequency.
Figure 5:
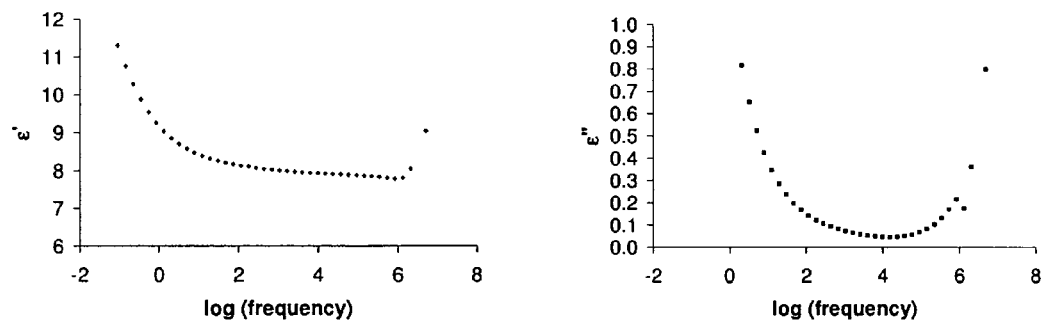
FIG. 5 shows the dielectric properties of a sample that was polymerized using BF$_3$ etherate and was not water washed.

At 1 kHz, a pressed pellet of the acetone insoluble fraction of JP-30-A had a dielectric constant of 7. As indicated in FIG. 4, the dielectric constant decreases linearly with the log of the frequency up to nearly 2 GHz, and the loss factors increase dramatically above 5 MHz. DC resistivity exceeded 4×10$^{10}$ Ω-cm. The dielectric constants, while high, are less than those observed in a series of propoxysulfolane pendant silicones (Purdy et al., *Polymeric Materials: Science and Engineering*, 84, 641 (2001)). However, the loss factors are also much less. The greater rigidity of the backbone and shortness of the pendant groups, and possibly less ionic contamination, probably accounts for the difference. FIG. 5 shows the dielectric properties of a sample that was polymerized using BF$_3$ etherate and was not water washed. It may contain ionic impurities that cause the higher losses at the lowest frequencies.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:
1. A compound comprising the formula:

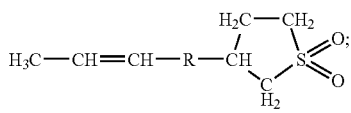

wherein R is —O—, —O—R'—O—, or —R"—O—;
wherein R' is an alkyl chain; and
wherein R" is a polyethylene glycol chain having one or more repeat units.

2. The compound of claim 1, wherein the compound is:

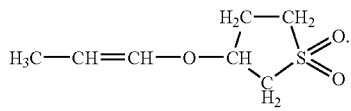

3. The compound of claim 1, wherein the compound comprises a mixture of cis and trans isomers.

4. A compound comprising the formula:

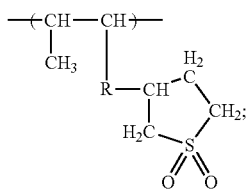

wherein R is —O—, —O—R'—O—, or —R"—O—;
wherein R' is an alkyl chain; and
wherein R" is a polyethylene glycol chain having one or more repeat units.

5. A capacitor comprising a dielectric material comprising the compound of claim 4.

6. The compound of claim 4, wherein the compound is:

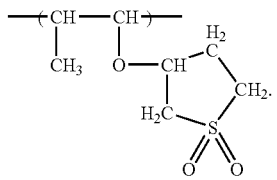

7. A capacitor comprising a dielectric material comprising the compound of claim 6.

8. A method comprising:
providing an allyl ether compound comprising the formula:

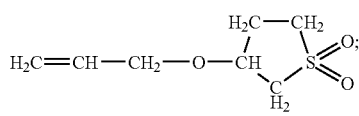

wherein R is —O—, —O—R'—O—, or —R"—O—;
wherein R' is an alkyl chain; and
wherein R" is a polyethylene glycol chain having one or more repeat units; and heating the allyl ether compound in the presence of $Fe(CO)_5$ and a base to form a propenyl ether monomer comprising the formula:

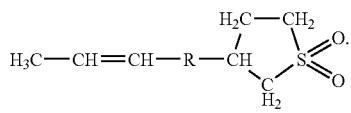

9. The method of claim 8, further comprising:
purifying the propenyl ether monomer by treatment with copper sulfate solution.

10. The method of claim 8, further comprising:
polymerizing the propenyl ether monomer.

11. The method of claim 8, wherein the allyl ether compound is:

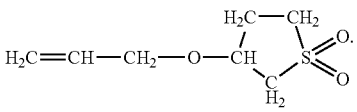

12. The method of claim 11, further comprising:
polymerizing the propenyl ether monomer.

13. A method comprising:
polymerizing a propenyl ether monomer comprising the formula:

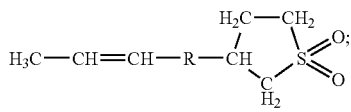

wherein R is —O—, —O—R'—O—, or —R"—O—;
wherein R' is an alkyl chain; and
wherein R" is a polyethylene glycol chain having one or more repeat units.

14. The method of claim 13, wherein the polymerizing is performed by photopolymerization.

15. The method of claim 13, wherein the polymerizing is performed in the presence of $BF_3(OEt_2)$.

16. The method of claim 13, wherein the propenyl ether monomer is:

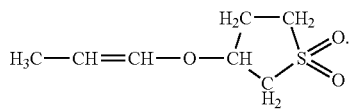

17. The method of claim 16, wherein the polymerizing is performed by photopolymerization.

18. The method of claim 16, wherein the polymerizing is performed in the presence of $BF_3(OEt_2)$.

* * * * *